US011353445B2

(12) United States Patent
Wrobel

(10) Patent No.: US 11,353,445 B2
(45) Date of Patent: Jun. 7, 2022

(54) METHOD AND DEVICE FOR DETERMINING AND/OR MONITORING THE STATE OF A TRANSFORMER OIL

(71) Applicant: PASSERRO GMBH, Leipzig (DE)

(72) Inventor: Matthias Wrobel, Munich (DE)

(73) Assignee: PASSERRO GMBH, Leipzig (DE)

( * ) Notice: Subject to any disclaimer, the term of this patent is extended or adjusted under 35 U.S.C. 154(b) by 360 days.

(21) Appl. No.: 16/331,754

(22) PCT Filed: Sep. 6, 2017

(86) PCT No.: PCT/EP2017/072286
§ 371 (c)(1),
(2) Date: Mar. 8, 2019

(87) PCT Pub. No.: WO2018/050499
PCT Pub. Date: Mar. 22, 2018

(65) Prior Publication Data
US 2019/0204289 A1 Jul. 4, 2019

(30) Foreign Application Priority Data
Sep. 13, 2016 (DE) .................... 10 2016 117 188.3

(51) Int. Cl.
*G01N 33/28* (2006.01)
*G01H 3/04* (2006.01)
(Continued)

(52) U.S. Cl.
CPC .............. *G01N 33/28* (2013.01); *G01H 3/04* (2013.01); *G01H 15/00* (2013.01);
(Continued)

(58) Field of Classification Search
CPC .... G01H 15/00; G01H 3/04; G01N 2291/011; G01N 2291/015; G01N 2291/0226;
(Continued)

(56) References Cited

U.S. PATENT DOCUMENTS 4,364,273 A * 12/1982 Redding ................ G01N 29/11
367/101
2015/0115983 A1 4/2015 Potyrailo et al.
(Continued)

FOREIGN PATENT DOCUMENTS

DE 19706486 A1 8/1998
DE 19850799 A1 5/2000
(Continued)

OTHER PUBLICATIONS

PCT International Search Report, PCT/EP2017/072286, dated Dec. 13, 2017, 6 pages.
(Continued)

*Primary Examiner* — John Fitzgerald
*Assistant Examiner* — Truong D Phan
(74) *Attorney, Agent, or Firm* — Quarles & Brady LLP

(57) ABSTRACT

The disclosure relates to a method for determining and/or monitoring the state of a transformer oil, comprising the steps of
a) performing an acoustic spectroscopy of the transformer oil, multiple ultrasonic emission signals of different frequencies and/or amplitudes being emitted into the transformer oil and corresponding reflected and/or transmitted ultrasonic reception signals of different frequencies and/or amplitudes being received after having passed through the transformer oil; and
b) comparing the ultrasonic emission signals with the corresponding ultrasonic reception signals, an n-dimensional function characteristic of the transformer oil being ascertained; and
c) matching the ascertained characteristic n-dimensional function from step b) with a reference function of corresponding dimension known for transformer oils, a reference transformer oil being determined; and
(Continued)

Figure 1:
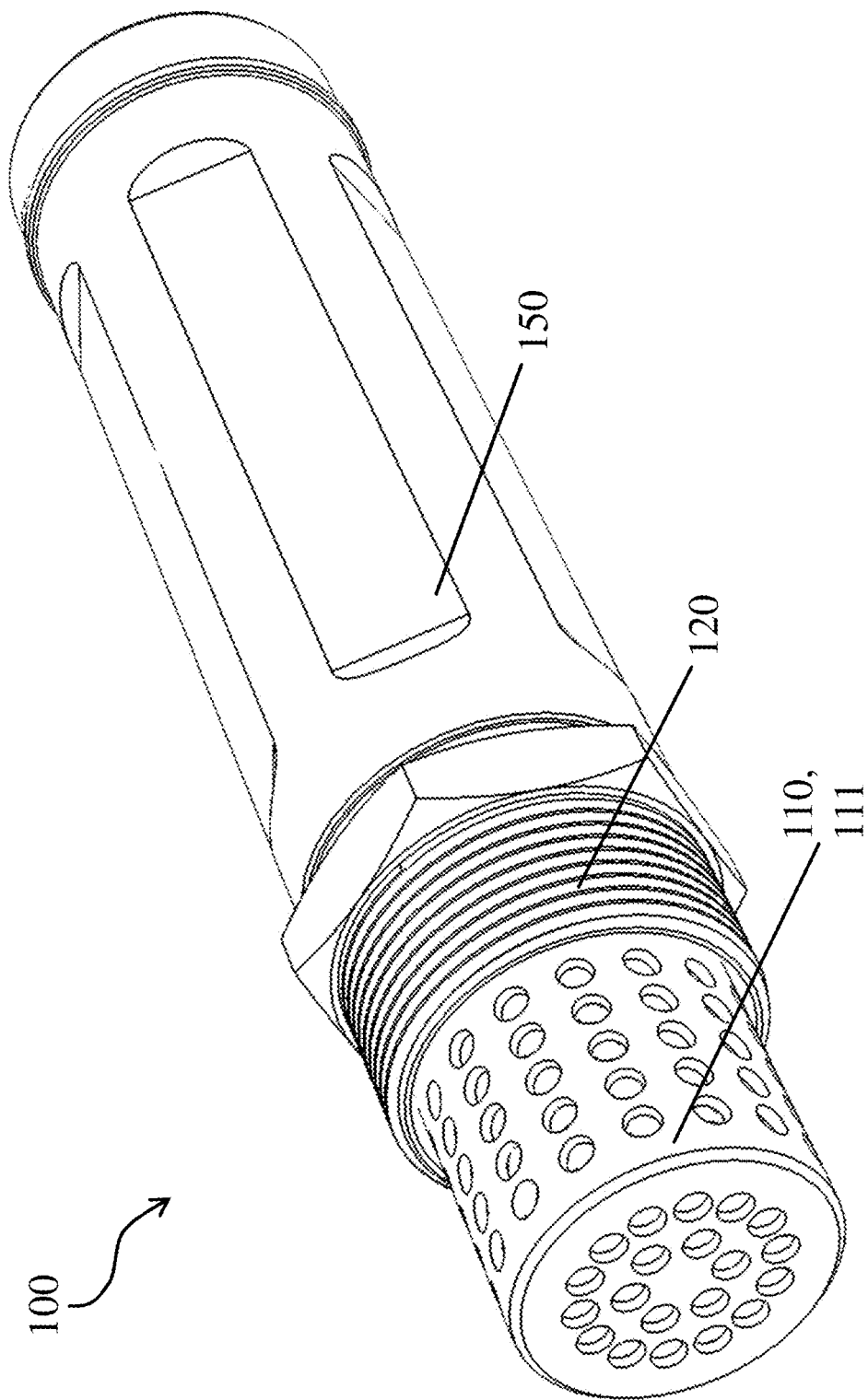

d) registering a first value of at least one characteristic physical property of the transformer oil; and
e) comparing the first value with a corresponding value of the reference transformer oil; and
f) ascertaining the state of the transformer oil based on the comparison performed in step e).

Furthermore, the disclosure relates to a device (100, 200) for determining and/or monitoring the state of a transformer oil.

17 Claims, 8 Drawing Sheets

(51) Int. Cl.
*G01N 29/024* (2006.01)
*G01N 29/032* (2006.01)
*G01N 29/34* (2006.01)
*G01N 29/44* (2006.01)
*G01H 15/00* (2006.01)

(52) U.S. Cl.
CPC ......... *G01N 29/024* (2013.01); *G01N 29/032* (2013.01); *G01N 29/346* (2013.01); *G01N 29/348* (2013.01); *G01N 29/4436* (2013.01); *G01N 2291/011* (2013.01); *G01N 2291/015* (2013.01); *G01N 2291/0226* (2013.01); *G01N 2291/044* (2013.01)

(58) Field of Classification Search
CPC ........... G01N 2291/044; G01N 29/024; G01N 29/032; G01N 29/346; G01N 29/348; G01N 29/4436; G01N 33/28; G01N 29/225; G01N 29/226; G01N 29/223; G01N 29/26; G01N 29/265

See application file for complete search history.

(56) References Cited

U.S. PATENT DOCUMENTS

2016/0169839 A1* 6/2016 Gottlieb ................. G01F 22/00
367/7
2018/0266996 A1* 9/2018 Fokow ............... G01N 33/2847

FOREIGN PATENT DOCUMENTS

DE 102013005003 A1 9/2014
DE 102014104963 A1 10/2014
DE 102015122926 A1 6/2016

OTHER PUBLICATIONS

PCT English Language Translation of the International Preliminary Report on Patentability, PCT/EP2017/072286, dated Mar. 28, 2019, 8 pages.

* cited by examiner

METHOD AND DEVICE FOR DETERMINING AND/OR MONITORING THE STATE OF A TRANSFORMER OIL

CROSS-REFERENCE TO RELATED APPLICATIONS

This application represents the national stage entry of PCT International Application No. PCT/EP2017/072286 filed Sep. 6, 2017, which claims priority of German Patent Application 10 2016 117 188.3, filed Sep. 13, 2016, the contents of which are hereby incorporated by reference as if set forth in their entirety herein for all purposes.

The disclosure relates to a method and to a device for determining and/or monitoring the state of a transformer oil according to the preambles of the independent claims.

Devices of high-voltage technology, such as transformers, capacitors, Petersen coils and/or switches, are known from the state of the art and serve in particular, but by no means exclusively, to ensure a continuous electrical energy supply. Among these devices, transformers belong to the most important and also most expensive pieces of equipment in the electrical energy supply. To ensure a continuous and fault-free supply of electrical energy and to avoid economic losses, it is important that malfunctions which potentially occur in the operation of a transformer and which can cause outages are detected in time so as to be able to initiate suitable measures for rectification.

Typically, a combination of a liquid insulating material and a solid insulating material is used as insulant in transformers. For example, but by no means exclusively, the solid insulant is cellulose paper and/or chipboard. The liquid insulant, the transformer oil, is stable even at high temperatures and is used for insulation, spark suppression, lubrication and/or cooling of the transformer. In liquid-filled transformers of this kind in particular, defects in the solid and/or liquid insulant are almost exclusively due to the formation of gasses dissolved in the transformer oil and to a resulting increase in water content. One reason for the formation of the gasses is the decomposition of solid and/or liquid insulating materials, for example, which can be caused by partial discharge and circulating currents, local overheating due to short circuits, high transition resistance, strong eddy currents, and by arc discharges and/or arcing. The electrical and/or thermal energy input leads to a destruction of the long-chain oil molecules, which produces hydrogen and light hydrocarbon compounds, in particular. Additionally, the decomposition of cellulose produces carbon monoxide and carbon dioxide, which can occur in dissolved and/or undissolved form depending on the amount of the produced gasses. Thus, water molecules may be produced, as well, which lead to the undesired moisture content in the oil.

The water contained in the transformer oil is also problematic because the water enters the solid insulant, such as cellulose paper and/or chipboard, and washes the acids contained therein from production out into the transformer oil. This puts additional strain on the transformer, said strain being alternately strong or weak for various reasons, such as daytime-related temperature fluctuations (e.g., between day and night).

Hence, in order to maintain functionality and/or to ensure a continuous electrical energy supply, it is important to determine and/or monitor the state of the transformer oil and of the transformer. Thus, it is no surprise that a multitude of different methods and devices for monitoring the state of transformer oils are known from the state of the art, which determine the gasses dissolved in the transformer oil and/or the water content, for example, because both are known to have substantial impact on the breakdown voltage and thus indirectly on the life span and/or utilization time of the transformer. The reason for this is that water in the transformer leads to hydrolysis of the solid insulant and thus to a reduction of its degree of polymerization. However, all of these methods and devices have the disadvantage that sampling is required and that the state of the transformer oil is determined and/or monitored neither permanently nor on-line. It is not possible either to detect load peaks of the transformer in this way. Another problem with this is that transformer oil is highly hygroscopic, which means that sampling itself will distort the measured values.

Hence, there is great demand for a method and for a device for determining and/or monitoring the state of a transformer oil and thus indirectly for determining and/or monitoring the state of a device of high-voltage technology by means of which quick, reliable and sufficiently precise determination and/or monitoring of the state is ensured so as to avoid an unnecessary and expensive oil change and simultaneously ensure the continuous electrical energy supply. Moreover, the method and the device should be cost-effective in terms of implementation, work reliably, and be suitable for permanent determination and/or monitoring. Hence, the object of the disclosure is to provide a method and a device for determining and/or monitoring the state of a transformer oil in order to overcome the above-mentioned challenges and, above all, avoid a premature and/or unnecessary oil change and to ideally plan oil regeneration and/or maintenance and/or repair-related work so as to reduce downtimes of the device and the resulting costs to a minimum.

This object is attained in a surprisingly simple but effective manner by a method for determining and/or monitoring the state of a transformer oil and by a corresponding device according to the teaching of the independent main claims.

The disclosure proposes a method for determining and/or monitoring the state of a transformer oil that comprises the following steps:

a) performing an acoustic spectroscopy of the transformer oil, multiple ultrasonic emission signals of different frequencies and/or amplitudes being emitted into the transformer oil and corresponding reflected and/or transmitted ultrasonic reception signals of different frequencies and/or amplitudes being received after having passed through the transformer oil; and b) comparing the ultrasonic emission signals with the corresponding to ultrasonic reception signals, an n-dimensional function characteristic of the transformer oil being ascertained; and c) matching the ascertained characteristic n-dimensional function from step b) with a reference function of corresponding dimension known for transformer oils, a reference transformer oil being determined; and d) registering a first value of at least one characteristic physical property of the transformer oil; and e) comparing the first value with a corresponding value of the reference transformer oil; and f) ascertaining the state of the transformer oil based on the comparison performed in step e).

The method according to the disclosure is based on the idea that the combination of acoustic spectroscopy and of the registration of a first value of at least one characteristic physical property of the transformer oil suffices in order to determine and/or monitor the state of a transformer oil to sufficient precision. According to the disclosure, the transformer oil is first classified by means of acoustic spectroscopy by comparing the ultrasonic emission signals with the corresponding ultrasonic reception signals. Based on this comparison of the corresponding pairs of emission and reception signals, an n-dimensional function characteristic of the transformer oil is ascertained, which is then matched with a reference function of corresponding dimension known for transformer oils. In this way, it is possible to determine for the transformer oil a corresponding reference transformer oil that has known and defined physical properties. Based on this classification, it is sufficient to register an actual value of a characteristic physical property of the transformer oil and to compare it to the corresponding target value of the reference transformer oil so as to determine the state of the transformer oil in a sufficiently precise manner. In connection with the disclosure, it was found that the method is suitable for permanent determination and/or monitoring of the state of the transformer oil, the mere testing of the transformer oil being sufficient and sampling with its known disadvantages being entirely unnecessary.

The term "method for determining and/or monitoring the state" refers to a method for ascertaining the state of the transformer oil which allows an assessment of the remaining useful life, the age, the breakdown voltage and/or the imminence of a transformer oil change or of a corresponding transformer oil regeneration. It is conceivable that the determination is performed once or repeatedly. Preferably, the method is based on ascertaining the change, preferably an improvement or a deterioration, of at least one characteristic physical property of the transformer oil. More preferably, said change is ascertained over time, preferably over the utilization time, the service life, and/or the downtime. Further preferably, the state of the transformer oil is determined at regular or irregular intervals or permanently so as to be able to quickly detect the change of the at least one property. This is important in particular because transformer oil is not a static system. Additionally, the conditions and/or influences under which the change of the at least one property of the transformer oil progresses or slows down can be tracked. Moreover, the development and/or cause of said change can be identified, allowing ideal planning and/or prediction of an upcoming maintenance interval and/or an upcoming transformer oil change or a corresponding transformer oil regeneration. In this regard, the method according to the disclosure may comprise additional steps that take place after or between the explicitly listed essential steps a) to f). Preferably, the method can be automated.

The term "determining the state" of the transformer oil refers to ascertaining the current state of the transformer oil. Determination is preferably performed semi-quantitatively, quantitatively, directly and/or indirectly. For instance, it is possible to ascertain the state of the transformer indirectly by ascertaining the breakdown voltage of the transformer oil.

The term "monitoring the state" refers to the tracking and/or prediction of the ascertained state of the transformer oil. For example, but by no means exclusively, monitoring can be displayed numerically and/or graphically. To increase the preciseness of monitoring, it preferably takes place at regular or irregular intervals or permanently. The advantage of longer monitoring is that a prediction of the state of the transformer oil is drastically improved.

A person skilled in the art understands that determination and/or monitoring will typically not be 100 percent correct. The term thus relates to a statistically significant probability regarding the preciseness of the ascertainment of the state and of the tracking and/or prediction of the ascertained state. A skilled person can determine whether such a determination and/or monitoring is statistically significant by methods known in the professional world without taking an inventive step. For example, statistical evaluation tools are to be mentioned, such as determination of the confidence interval, the p-value, the Student's t-test, the Mann-Whitney test, etc. The corresponding intervals are at least 90%, at least 95%, at least 97%, at least 98%, or at least 99% correct. The p-values are preferably 0.1, 0.05, 0.01, 0.005, or 0.0001. In connection with the disclosure, determination and/or monitoring of the state is preferably at least 80%, at least 90%, at least 95%, at least 96%, at least 97%, at least 98%, at least 99%, at least 99.5%, or 100% correct.

The method according to the disclosure comprises a step a) for performing an acoustic spectroscopy of the transformer oil, multiple ultrasonic emission signals of different frequencies and/or amplitudes being emitted into the transformer oil and corresponding reflected and/or transmitted ultrasonic reception signals of different frequencies and/or amplitudes being received after having passed through the transformer oil. In another step, the ultrasonic emission signals are compared with the corresponding ultrasonic reception signals, an n-dimensional function characteristic of the transformer oil being ascertained. In this regard, the running time and/or the frequency shift of the matched ultrasonic signal are ascertained from each pair of emission and reception signals. Additionally, the damping of the matched ultrasonic signal, preferably its amplitude, is ascertained from each pair of emission and reception signals during passage through the transformer oil. In other words, this means that from each pair of emission and reception signals of a corresponding or specific frequency, a data pair composed of the respective running times, the frequency shifts and/or the respective damping is ascertained as a result by means of the method according to the disclosure.

In connection with the present disclosure, it was found that not all data have to be registered in order to characterize a pair of emission and reception signals. For instance, but by no means exclusively, it is not necessary to know the phase of the emission signal because the phase of the emission signal is not needed to ascertain the running time and/or the frequency shift and the reception of the emission signal during passage through the transformer oil. Merely the data for characterizing the emission and reception signals that are relevant for ascertaining the running time, the frequency shift and/or the damping have to be registered. This is because changes in the transformer oil will reflect significantly in the result data pair composed of running time, frequency shift and/or damping, which is why the dispersity of the tested transformer oil can also be ascertained based on the measurement of the running time and/or of the frequency shift. The combination of the measurement of damping and dispersity of the tested material allows a highly nuanced characterization of the tested material.

According to the disclosure, a data pair composed of the respective running times, the frequency shifts and/or the respective damping is ascertained as a result from each pair of emission and reception signals of a corresponding or specific frequency by means of the method according to the disclosure and may be stored in connection with the corresponding frequency in a device configured accordingly. During implementation of the method, extensive sets of result data are accumulated because a set of result data including the respective running times, the frequency shifts and/or the respective damping is determined, stored and/or graphically displayed for each frequency and the matching pair of emission and reception signals. Hence, it is preferably envisaged that data reduction is performed; for example, a reduced set of result data is derived from the ascertained set of result data in a data reduction unit, the reduced set of result data characteristically representing the ascertained set of result data and having smaller data volume. The manner in which data reduction is performed is basically optional and is subject to the skilled person's expertise.

The term "acoustic spectroscopy" refers to the acoustic test of a fluid by drawing conclusions from the changes of acoustic waves and/or vibrations in the ultrasonic frequency range (20 kHz to 1 GHz), the changes being based on the interactions between the molecules contained in the fluid and the acoustic waves and/or the vibrations. In this way, it is possible to use the acoustic spectroscopy to test the composition of the fluid and to draw conclusions as to the composition of the fluid. The fluid to be tested in connection with the disclosure is preferably a transformer oil. Preferably, the acoustic spectroscopy is performed with the aid of a suitable medium that is partially or entirely disposed in the fluid and that is capable of emitting vibrations, of transmitting vibrations, of amplifying vibrations and/or of receiving vibrations in the fluid, such as an ultrasonic emitter and/or receiver. Furthermore, it is conceivable that the first medium is a resonator, a resonance body, a resonance chamber, a converter or a combination of all of the aforementioned devices.

Preferably, the acoustic spectroscopy refers to ultrasonic frequencies, more preferably to frequencies of 75 kHz to 750 kHz. Further preferably, the acoustic spectroscopy is performed in at least one frequency band. More preferably, the acoustic spectroscopy is performed in two, three, four, five, six, seven, eight, nine, ten, or more frequency bands, wherein it was found to be a substantial aspect in connection with the disclosure that each frequency band has a defined frequency width in a defined frequency range. Hence, it is understandable that each frequency band has the same frequency width. For example, but by no means exclusively, it is possible to perform the acoustic spectroscopy in four frequency bands each having the defined frequency width of 75 kHz in the defined frequency range of 75 kHz to 750 kHz, such as in the manner of frequency band 1 (125 kHz to 200 kHz), frequency band 2 (225 kHz to 300 kHz), frequency band 3 (325 kHz to 400 kHz) and frequency band 4 (525 kHz to 600 kHz). Preferably, a new measurement is performed at the frequency that corresponds to the defined frequency width of 75 kHz per frequency band.

According to the disclosure, it is envisaged that it is possible based on the comparison of the corresponding pairs of emission and reception signals, preferably based on the obtained corresponding sets of result data, to ascertain an n-dimensional function characteristic of the transformer oil, such as the acoustic disbalance (AcDis). A person skilled in the art knows what an n-dimensional function is. Furthermore, the ascertained characteristic n-dimensional function is matched with a reference function of corresponding dimension known for transformer oils, a reference transformer oil having defined and known physical properties being determined. For example but by no means exclusively, the reference function is stored in a data archive.

In connection with the disclosure, the term "reference function" or "reference transformer oil" refers to a reference value that is, in particular, but by no means exclusively, an ascertained and/or theoretical value, such as a lab value and/or a data archive entry, and is registered prior to first use of the of the transformer oil. Furthermore, it is conceivable that a reference value of this kind defines a threshold which is preferably defined as an upper limit of the normal value of the corresponding physical property under different conditions. The value of the upper limit of the normal value can be determined by means of different techniques well known to a person skilled in the art.

Subsequently, a first value of at least one characteristic physical property of the transformer oil is registered and compared to a corresponding value of the reference transformer oil, the state of the transformer oil and of the transformer being ascertained based on said comparison.

The term "characteristic physical property" refers to a physical property that is typical of the transformer oil and from which the state of the transformer oil and of the transformer can be concluded directly or indirectly. Preferably, said property changes as a function of the aging process of the transformer oil, the change preferably being an improvement or a deterioration. In this regard, it is important that the property is known from the reference transformer oil and/or defined precisely enough for its change, such as over time, to be used to determine and/or monitor the state. The functional correlation can be represented, for example, but by no means exclusively, as a trend with a value curve over time in a 2-dimensional function, such as in a linear function, in a logarithmic function, in an exponential function, in a logistic function, in a polygonal function and/or in a mixture thereof.

In connection with the disclosure, it was found to be a substantial aspect that the combination of acoustic spectroscopy and registration of a first value of a characteristic physical property is sufficient. It is conceivable that 2, 3, 4, 5, 6, 7, 8, 9, 10, 11, 12, 13, 14, 15, 16, 17, 18, 19, 20 or more values of the same characteristic physical property are registered. Preferably, it is conceivable that a mean value is used for further comparison of said value with the corresponding value of the reference transformer oil. Alternatively, it is also conceivable that 2, 3, 4, 5, 6, 7, 8, 9, 10, 11, 12, 13, 14, 15, 16, 17, 18, 19, 20 or more values of different characteristic physical properties are registered. This is because a physical property depends on and/or can be influenced by different factors, whose additional registration adds to further improvement of the determination and/or monitoring. For instance, temperature, pressure, color, refractive index and/or saturation can be contemplated in this context.

The term "comparison" as used herein refers to the comparison of mutually corresponding values among each other, in particular of the ultrasonic emission signal with the corresponding ultrasonic reception signal or of the first value of at least one characteristic physical property of the transformer oil with the corresponding value of the reference transformer oil. It is understood that a comparison as used herein refers to a comparison of corresponding parameters and/or values. For instance, it is conceivable that an absolute first value of the characteristic physical property is compared to an absolute corresponding value of the reference transformer oil. The same applies to relative values, an intensity signal and/or an ultrasonic signal. It also conceivable for the comparison to be performed based on an empirically ascertained model for reference transformer oils.

In connection with the disclosure, the comparison, the matching, the registration and/or the ascertainment are preferably performed with computer assistance. For a computer-assisted performance of these steps, such as steps b), c), e) and/or f), all means known to the skilled person are conceivable, such as computers and/or a computer program. A computer program can additionally evaluate the corresponding result, automatically providing an assessment of the value, for example. Matching of the corresponding characteristic n-dimensional function of the transformer oil with a reference function is possible preferably by means of the comparison performed in step b). Furthermore, ascertainment of the state of the transformer oil is possible preferably by means of the comparison performed in step e). Furthermore, it is conceivable, for example, that the steps b), c), e) and/or f) are supported by an assessing unit, an analyzing unit, and/or an evaluating unit. Preferably, it is also possible to take successive values of a characteristic physical property or ultrasonic emission and/or reception signals into account in the comparison, allowing a prediction as to how the state will change as a function of time based on said comparison.

In connection with the disclosure, it is understood that the result of the comparison, i.e., the ascertainment and/or evaluation of the state of the transformer oil, depends directly or indirectly on the matching of the characteristic n-dimensional function with the reference function and the characteristic physical property. Thus, it is conceivable that a small and insignificant change, a great and significant change and/or no change of the first value of the characteristic physical property of the transformer oil with respect to the corresponding value of the reference transformer oil is indicative of a specific state. A change in the characteristic physical property can preferably be an improvement and/or a deterioration of said values. In this context, it is conceivable that the result of the comparison can be outputted as an indication of time, such as in years, months, days, hours and/or minutes, as an absolute value and/or a relative value.

The term "transformer oil" refers to a liquid insulating material which is stable at high temperatures and which is used for insulation, spark suppression, lubrication and/or cooling of a device of high-voltage technology, such as a transformer, a capacitor and/or a switch. For example, but by no means exclusively, the liquid insulating material is a highly refined mineral oil, a gas-to-liquid (GTL), a low-viscosity silicone oil, a natural oil, a vegetable oil, a synthetic organic ester, such as a saturated pentaerythritol tetra-fatty acid ester, and/or an amino-acid compound.

Thus, by means of the method according to the disclosure, it is possible to easily, quickly and reliably determine and/or monitor the state of the transformer oil in order to, for example, make an assessment regarding the state of the corresponding device of high-voltage technology. It is possible to perform this determination and/or monitoring in a running device, i.e., on-line. Advantageously, the method is designed in such a manner that sampling with its known disadvantages can be entirely omitted. In this way, it is possible to avoid premature and/or unnecessary and expensive oil change and to simultaneously ensure a continuous electrical energy supply at all times. Additionally, it is possible to ideally plan the downtimes of the device required for maintenance, regeneration and/or repair so as to avoid unnecessary downtimes and/or costs.

Advantageous embodiments of the disclosure, which can be realized individually or in combination, are illustrated in the dependent claims.

In an embodiment of the disclosure, it is conceivable that the method additionally comprises the step of:

g) displaying the ascertainment performed in step f).

By means of this configuration, it is possible to numerically and/or graphically display the state of the transformer oil in order to achieve an easier understanding of the ascertainment in step f) in this way. A person skilled in the art knows suitable means for displaying an output of a value. For instance, but by no means exclusively, it is possible to display a remaining useful life, the breakdown voltage and/or the imminence of a transformer oil change or of a transformer oil regeneration. Step g) can be aided by an output unit.

In another configuration of the disclosure, it is conceivable that the method comprises an additional step d1) after step d):

d1) registering at least one second value of at least one characteristic physical property of the transformer oil.

Registration of a second value offers the advantage that improved approximation of the functional correlation of the corresponding property and thus drastic improvement of the registration in step f) are achievable. In this way, for example, but by no means exclusively, an improved assessment of the curvature of the function can be made, wherein the rule applies that the precision of the ascertainment in step d) and/or step d1) increases as the number of registered values grows. Preferably, the registration of a second value is conceivable in that a second value of a different characteristic physical property is registered. Alternatively preferably, it is conceivable that a second value of the property previously registered in step d) is determined.

In another configuration of the disclosure, it is conceivable that the density, the viscosity, the relative and/or absolute amount of an inhibitor and/or of an acid of the transformer oil and/or a mixture thereof are determined by means of acoustic spectroscopy. In connection with the disclosure, it was found that additional advantages of the method according to the disclosure arise from the wide range of application of acoustic spectroscopy. For instance, the determination of the relative and/or absolute amount of an inhibitor and/or of an acid, preferably a short-chain or long-chain acid not determinable by pH measurement, in the transformer oil is preferably important, which only takes place by sampling and subsequent titration as per the current state of the art. An inhibitor, such as diphenyl disulfite, is used to protect against corrosion, diphenyl disulfite binding corrosive sulfur in the transformer oil, for example, thus reliably preventing and/or suppressing the formation of sulfuric acid. However, inhibitors of this kind are typically highly toxic compounds, which is why the determination of their relative and/or absolute amount understandably involves significant effort and high cost. By means of the method according to the disclosure, however, they as well as others can be determined easily, quickly, reliably and without hazard, which once more underscores the enormous advantages of the method.

In yet another configuration of the disclosure, it is conceivable that the characteristic physical property is the speed of sound, the density, the color, the refractive index, the sound absorption, the temperature, the interfacial tension, the viscosity, the relative and/or absolute moisture or saturation, the loss factor, the acid number, the electric constant, the electrical conductivity, and/or the concentration of at least one fluid. The aforementioned characteristic physical properties are well known to the person skilled in the art, as is their determination and/or calculation. Additionally, other properties not listed here are conceivable.

Furthermore, it is conceivable that the state is selected from the list of remaining useful life, state of health, breakdown voltage and/or imminence of a transformer oil change or of a transformer oil regeneration.

The term "remaining useful life" refers to the ascertainment of the remaining time for which the transformer oil will maintain functionality, insulating capability and/or protective function for the corresponding device of high-voltage technology. By ascertaining this value, one can determine and/or monitor when the transformer oil will need to undergo maintenance, repair, regeneration and/or change, for example. Additionally, one can monitor how the functionality, insulating function and/or protective function of the transformer oil changes over time. The remaining useful life can preferably be displayed in the form of a unit of time, such as in years, months, days, hours and/or minutes and as a relative value.

The term "state of health" describes an ascertainment of the maximum age, functionality, insulating capability and/or protective function of the transformer oil and/or of the der probability of execution of the corresponding device, for example. These values allow conclusions to be drawn as to when maintenance, repair or regeneration and/or change is sensible and/or necessary, for example, in order to ensure that no health-related failures of the corresponding device and thus no outage of the electrical energy supply, accompanied by the corresponding economical disadvantages, occur. Preferably, the state of health can be displayed in the form of a unit of time, such as in years, months, days, hours and/or minutes and as a relative value.

The term "breakdown voltage", shortened to BDV, refers to the electrical field strength in the transformer oil that may exist at maximum without leading to electrical breakdown, electric arcs and/or arcing and the related outages and disadvantages. The breakdown voltage depends on different factors. The breakdown voltage can preferably be displayed graphically and/or in the form of an absolute value conforming to the current DIN standard, such as to DIN EN 60243-1:2012-05, for example.

The term "imminence of a transformer oil change or of a transformer oil regeneration" refers to the ascertainment of the time remaining until the transformer oil will have to undergo maintenance, repair, regeneration and/or change. For example, one can monitor how the functionality, the insulating capability and/or the protective function of the transformer oil change over time. The imminence of a transformer oil change or of a transformer oil regeneration can preferably be displayed in the form of a unit of time, such as in years, months, days, hours and/or minutes and as a relative value.

It is assumed that the definitions and/or explanations of the terms mentioned above apply to all aspects described hereinafter in this description, unless indicated otherwise.

Furthermore, according to the disclosure, a device for determining and/or monitoring the state of a transformer oil according to any one of the method claims is proposed, comprising the following steps:

a) a first medium for performing an acoustic spectroscopy of the transformer oil, the first medium comprising an ultrasonic emitter for emitting multiple ultrasonic emission signals of different frequencies and/or amplitudes into the transformer oil and an ultrasonic receiver for receiving corresponding ultrasonic reception signals of different frequencies and/or amplitudes reflected and/or transmitted after having passed through the transformer oil; and b) a first evaluating unit for comparing the ultrasonic emission signals with the corresponding ultrasonic reception signals, an n-dimensional function characteristic of the transformer oil being ascertained; and c) a first analyzing unit for matching the ascertained characteristic n-dimensional function from step b) with a reference function of corresponding dimension known for transformer oils, a reference transformer oil being determined; and d) a second medium for registering a first value of at least one characteristic physical property of the transformer oil; and e) a second evaluating unit for comparing the first value with a corresponding value of the reference transformer oil; and f) a second analyzing unit for ascertaining the state of the transformer oil based on the comparison performed in step e).

The device according to the disclosure is preferably self-learning and/or self-calibrating so that best possible determination and/or monitoring of the state of the transformer oil can be achieved.

The term "first medium" refers to any medium known to the skilled person from the state of the art that is capable of emitting vibrations, transmitting vibrations, amplifying vibrations and/or attenuating vibrations in a fluid in the ultrasonic frequency range (20 kHz to 1 GHz), the fluid to be tested preferably being a transformer oil. Preferably, the medium is partially or entirely disposed in the fluid. Preferably, the first medium is an ultrasonic emitter for emitting multiple ultrasonic emission signals of different frequencies and/or amplitudes into the transformer oil and/or an ultrasonic receiver for receiving corresponding ultrasonic reception signals of different frequencies and/or amplitudes reflected and/or transmitted after having passed through the transformer oil. Furthermore, it is conceivable that the first medium is a resonator, a resonance body, a resonance chamber, a converter or a combination of all of the aforementioned devices.

The term "second medium" refers to any medium known to the person skilled in the art that is capable of registering the characteristic physical property of the transformer oil at a point in time. Preferably, the point in time is registered simultaneously.

The term "evaluating unit" refers to a unit that is capable of comparing the registered signals, values and/or state values. Suitable evaluating units, such as a computer and/or a computer program, are known to the person skilled in the art. A computer program can additionally assess the result of the comparison.

The term "analyzing unit" refers to a unit capable of analyzing or ascertaining the state of the transformer oil. For example, the analyzing unit is a computer and/or a computer program.

The device according to the disclosure has the advantage that it exhibits sufficiently precise sensitivity for determining and/or monitoring the state of the transformer oil during operation, i.e., on-line, while simultaneously being robust enough to withstand the everyday conditions of a working transformer in the long term.

Advantageous embodiments of the disclosure, which can be realized individually or in combination, are illustrated in the dependent claims.

In an embodiment of the disclosure, it is conceivable that the device additionally comprises an output unit for displaying the ascertainment performed by means of the second analyzing unit. The term "output unit" refers to a unit which is capable of displaying the ascertained state. This configuration allows the state of the transformer oil to be numerically and/or graphically displayed so as to achieve easier understanding of the ascertainment in step f) in this way. The person skilled in the art knows a suitable output unit for displaying.

In another configuration of the disclosure, it is conceivable that the device comprises an additional medium for registering at least one second value of at least one characteristic physical property of the transformer oil. A medium of this kind for registering another state value is known to the person skilled in the art. Preferably, said medium is the same medium as in step d), i.e., the second medium. Alternatively preferably, said medium is a different medium from the one in step d), i.e., a third medium.

Furthermore, it is conceivable that the density, the viscosity, the relative and/or absolute amount of an inhibitor and/or of an acid of the transformer oil and/or a mixture thereof are determined by means of the first medium.

In an embodiment of the present disclosure, it is conceivable that the first medium and/or the second medium register the speed of sound, the density, the color, the refractive index, the sound absorption, the temperature, the interfacial tension, the viscosity, the relative and/or absolute moisture or saturation, the loss factor, the acid number, the electric constant, the electrical conductivity and/or the concentration of at least one fluid.

In yet another embodiment, it is conceivable that the state is selected from the list of remaining useful life, state of health, breakdown voltage and/or imminence of a transformer oil change or of a transformer oil regeneration.

In an alternative configuration, it is conceivable that the first medium, the second medium, the first evaluating unit, the second evaluating unit, the first analyzing unit, the second analyzing unit and/or the output unit are disposed in one component. This configuration offers the advantage that the device is compact and very easy do handle and easy to transport.

In an alternative configuration of this embodiment, it is conceivable that the component is a measuring chamber, a stick, and/or an adapter. This configuration offers the advantage that the device can be easily, quickly and reliably connected to a device of high-voltage technology, such as a transformer. Further preferably, the device is connected directly, such as by cable or via an adapter.

In another configuration, it is conceivable that the device comprises a heating device. This configuration has the advantage that the device can be heated prior to performing the first measurement, thus ensuring that the media located in the device are always dry. This helps improve the measured values significantly because distortions are typically due to the media being penetrated by moisture. Heating devices of this kind, such as a heating coil and/or a Peltier element, are well known to the person skilled in the art.

Furthermore, according to the disclosure, a device of high-voltage technology, in particular a transformer, a capacitor, a Petersen coil and/or a switch, comprising transformer oil and a means for connecting the same to the device according to any one of the preceding claims is proposed, the connection being a direct connection.

The term "direct connection" refers to any immediate connection of the means to the device. A connection of this kind can be realized, for example, but by no means exclusively, by way of a recess and/or a protrusion on the means and a correspondingly configured device. Furthermore, it is conceivable that a direct connection is a USB, TCP/IP, or MODBUS connection or any other wired or wireless connection. This configuration allows simple, quick and reliable connection of the device for determining the state of the transformer oil to a device of high-voltage technology in order to determine and/or monitor the state thereof in a quick, reliable and appropriately precise fashion.

Other details, features and advantages of the disclosure are apparent from the following description of the preferred embodiments in conjunction with the dependent claims. The respective features can be realized on their own or multiple features can be realized in combination with one another. The disclosure is not limited to the embodiments. The embodiments are schematically illustrated in the figures. Identical reference signs in the individual figures refer to identical elements or to elements of identical or mutually corresponding function.

Figure 2:
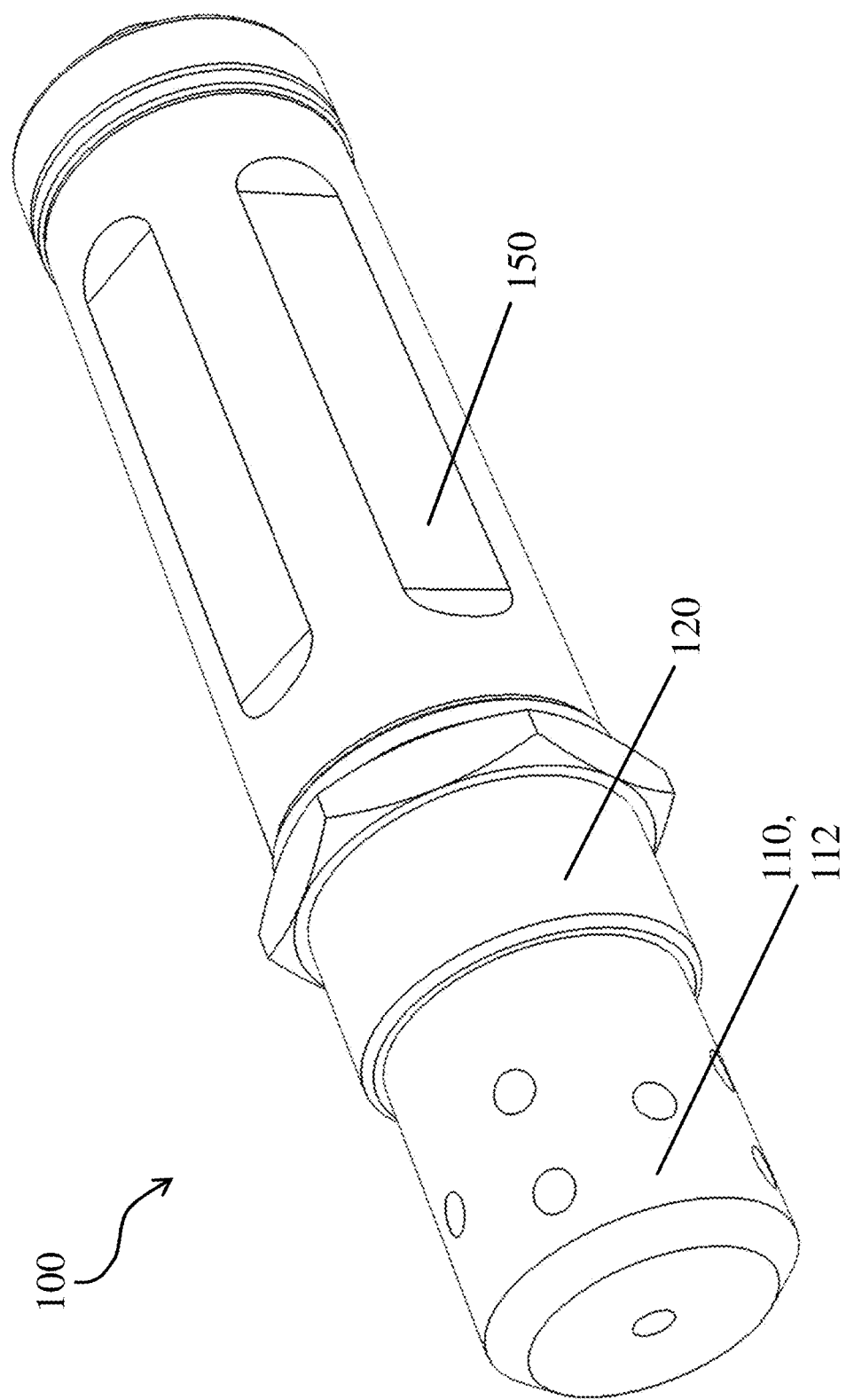
Figure 3:
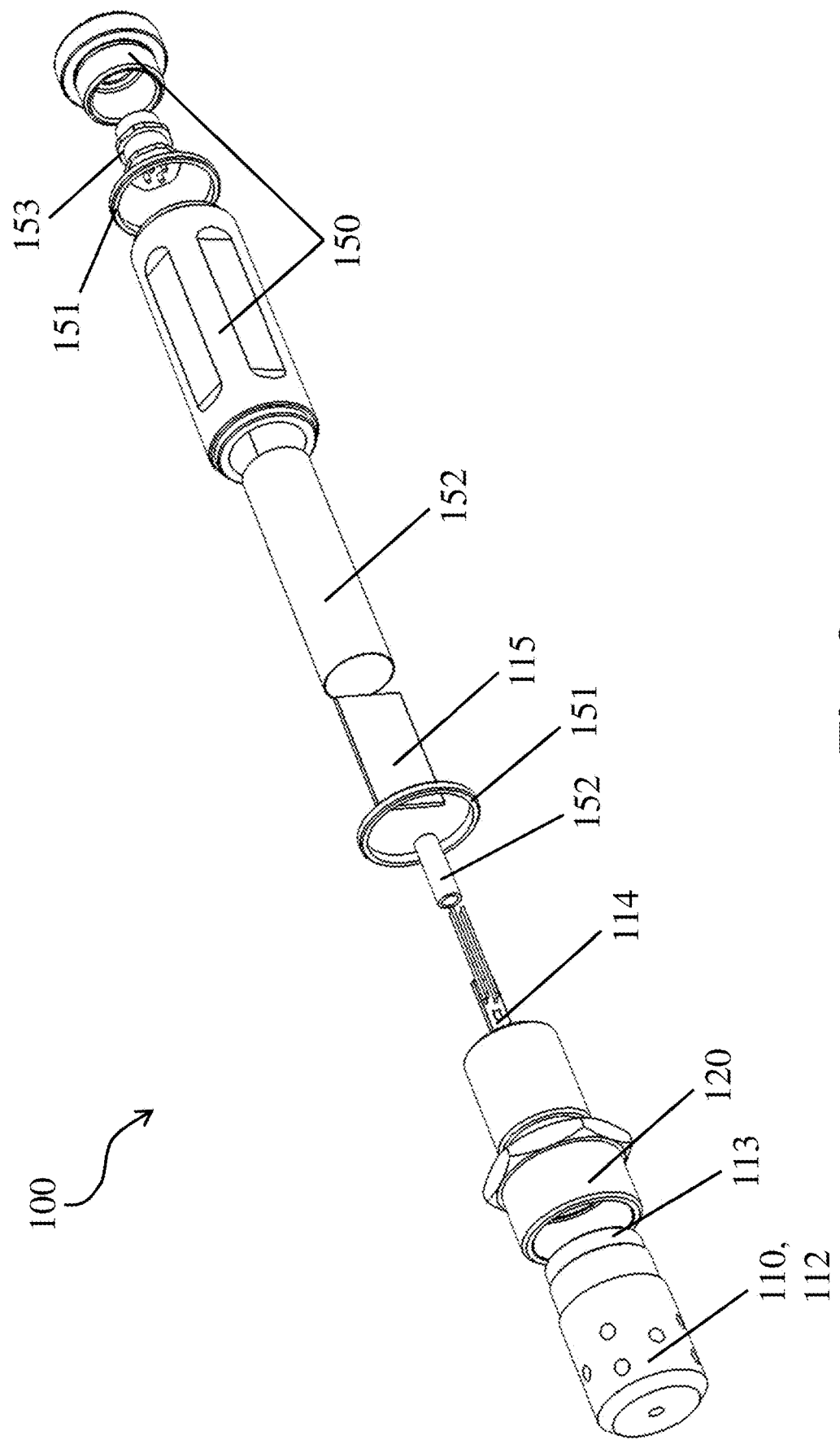
Figure 4:
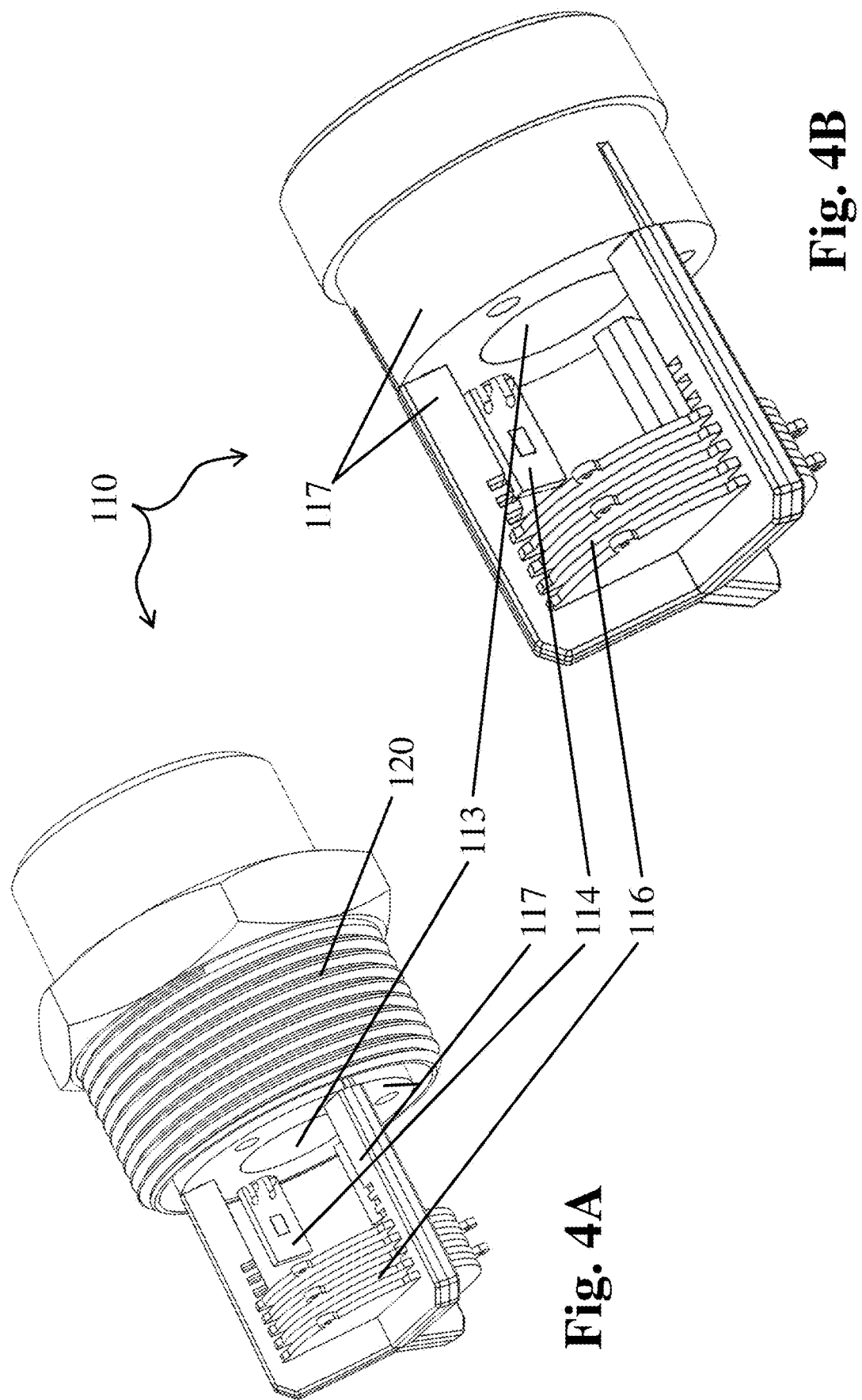
Figure 5:
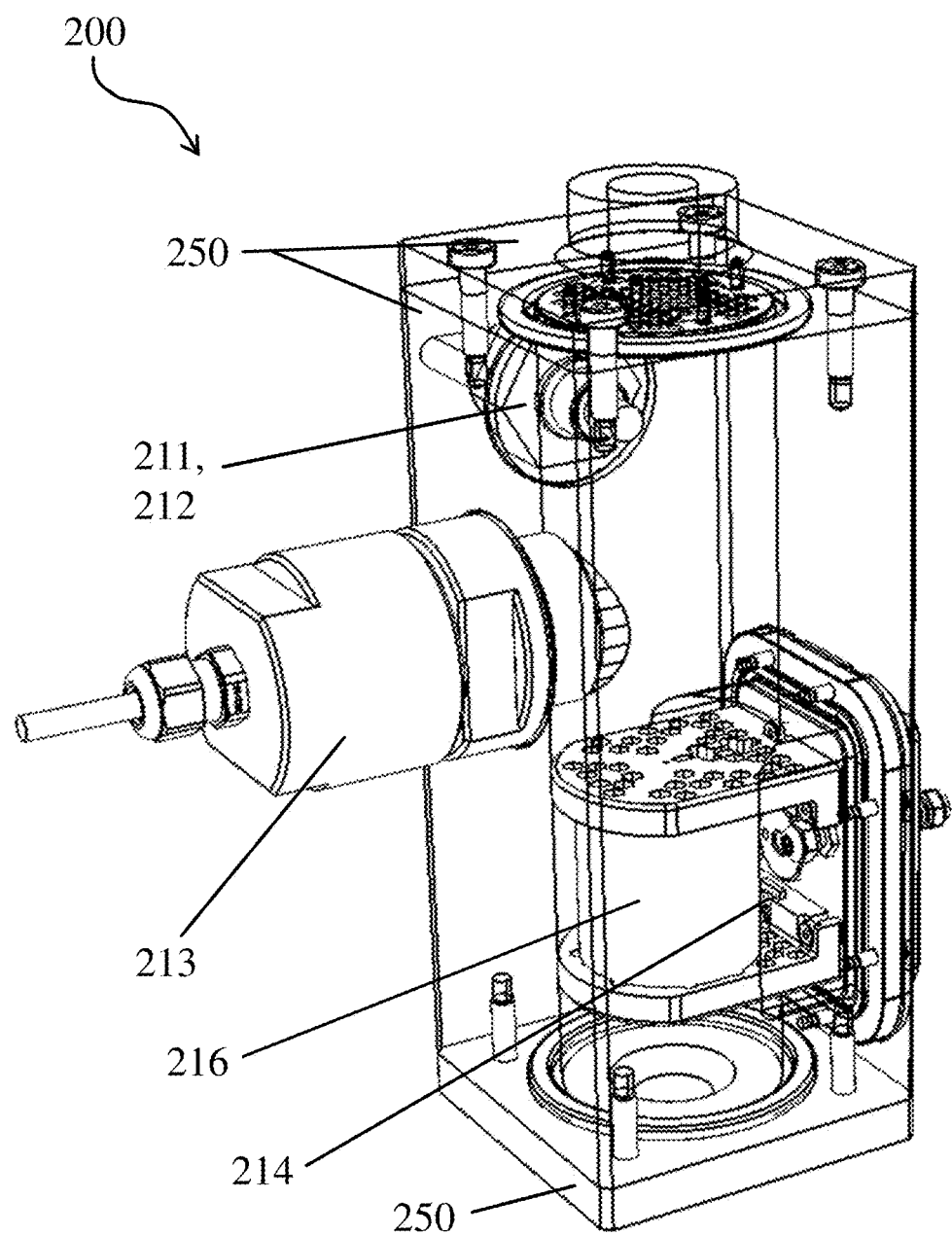
Figure 6:
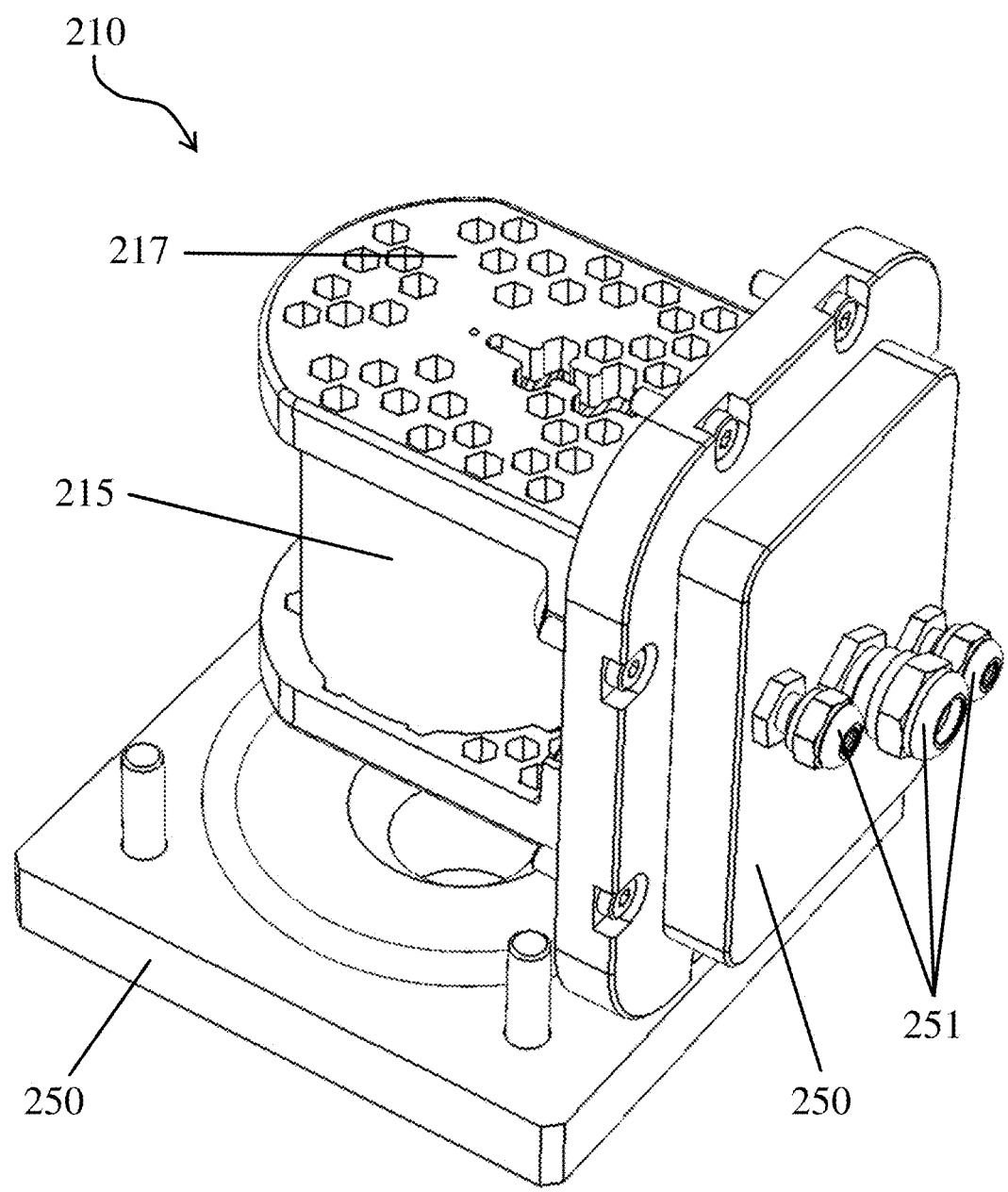
Figure 7:
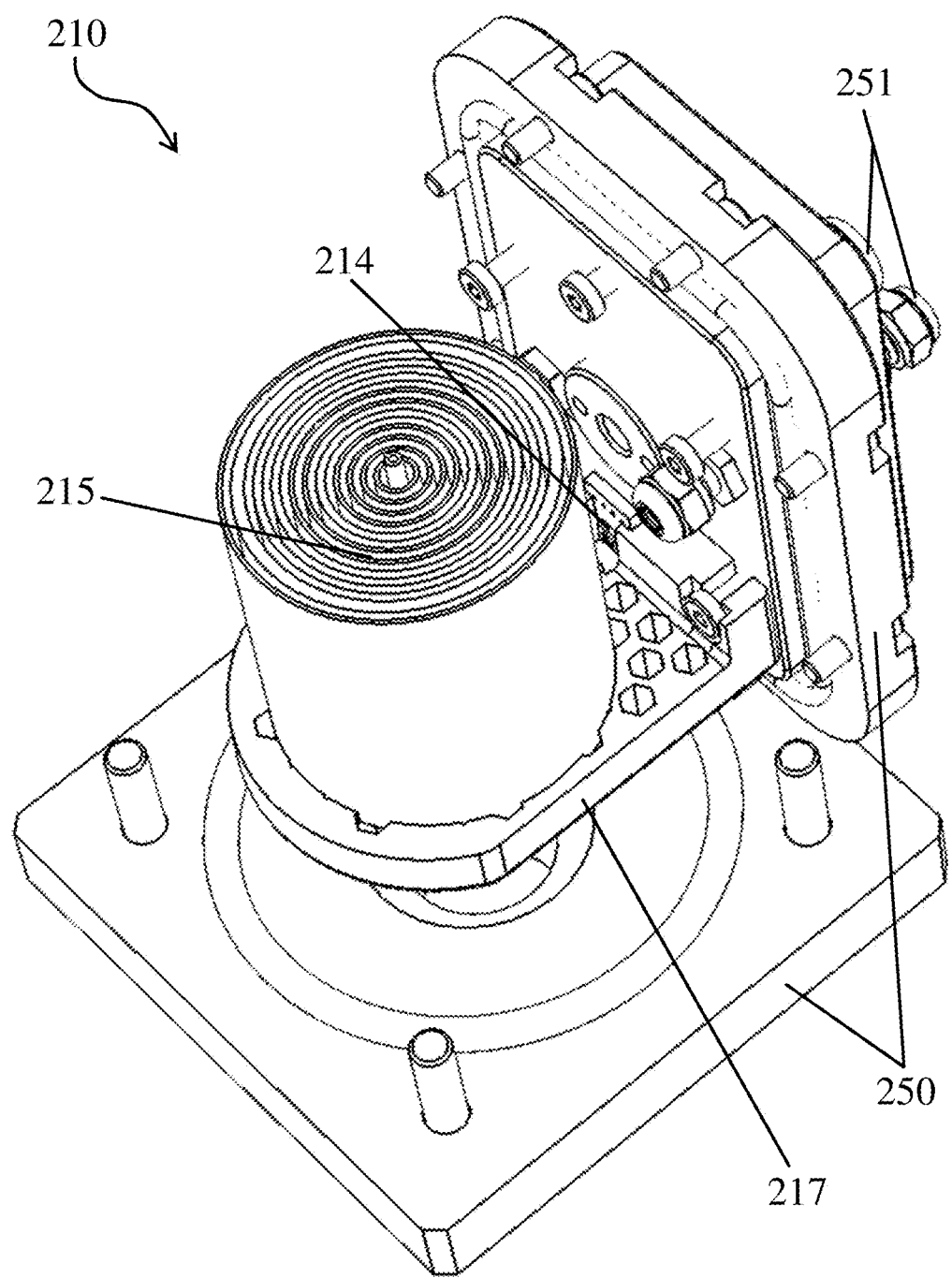
Figure 8:
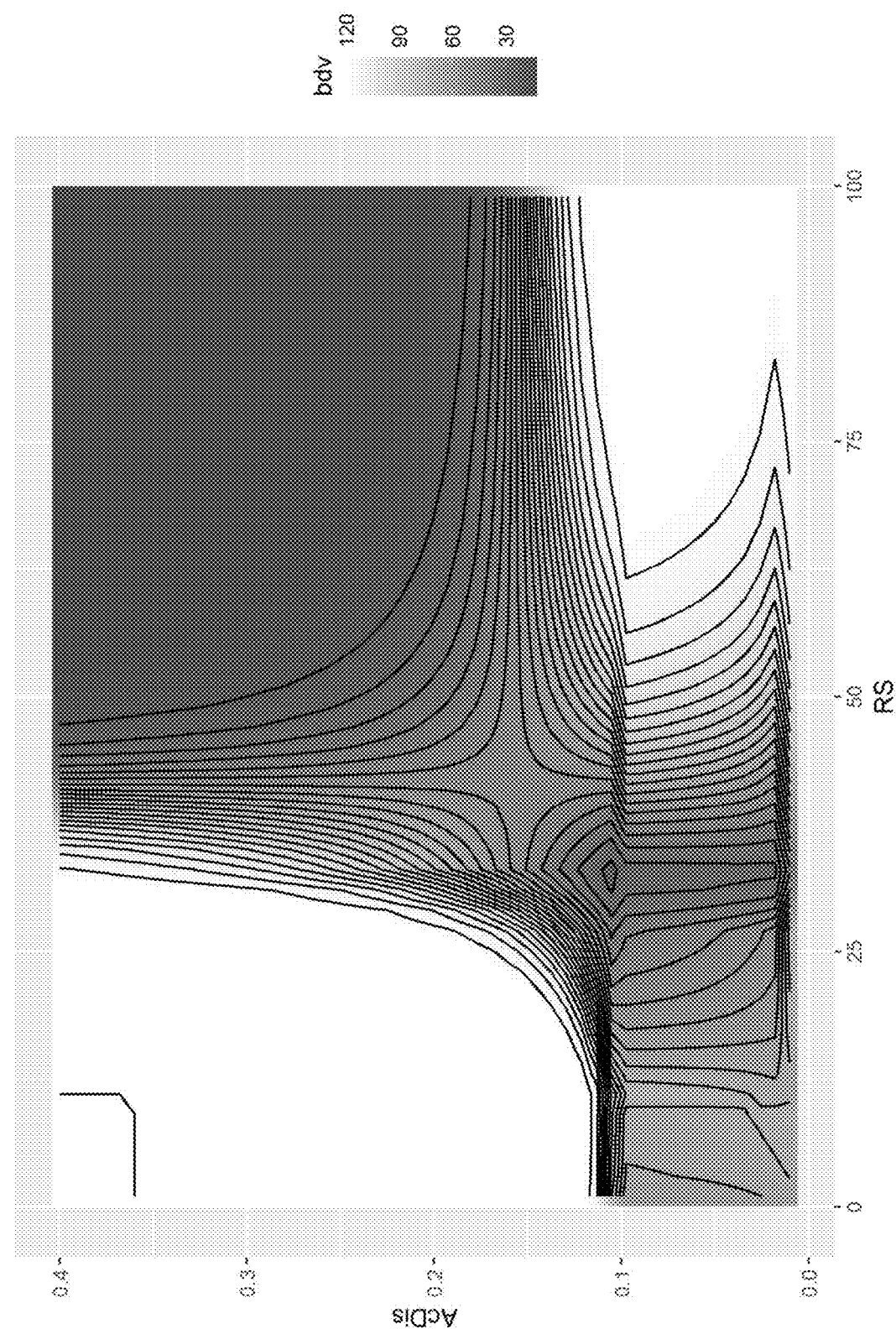

FIG. 1 shows an isometric illustration of a first embodiment of a device according to the disclosure with a protective cover; and FIG. 2 shows another isometric illustration of the first embodiment in a device according to the disclosure without a protective cover; and FIG. 3 shows an exploded illustration of the first embodiment of a device according to the disclosure without a protective cover; and FIG. 4 shows an isometric illustration of the sensor portion of the first embodiment of a device according to the disclosure with different attachment portions (FIGS. 4*a* and 4*b*); and FIG. 5 shows an isometric illustration of a second embodiment of a device according to the disclosure; and FIG. 6 shows an isometric illustration of a sensor portion of the second embodiment of a device according to the disclosure; and FIG. 7 shows another isometric illustration of a sensor portion of the second embodiment of a device according to the disclosure; and FIG. 8 shows a matrix graphic of an exemplary calculation of the determination of the breakdown voltage of a transformer oil.

FIG. 1 shows an isometric illustration of a first embodiment of a device 100 according to the disclosure for determining and/or monitoring the state of a transformer oil, the device 100 being realized in the form of a stick 100. As clearly visible in FIG. 1, stick 100 has a sensor portion 110 provided with a protective cover 111. Additionally, an attachment portion 120 for secure attachment of stick 100 to a transformer is provided on stick 100, said attachment portion 120 being realized in the form of a 1.5-inch pipe thread. Housing 150 of stick 100 protects the electronics, in particular against undesired electrical and/or electromagnetic effect, as well as serving as insulation and as a communication device and may be made from any suitable material. Preferably, housing 105 is made of a metallic material guaranteeing electromagnetic compatibility.

In FIG. 2, an alternative configuration of the first embodiment of a device 100 according to the disclosure for determining and/or monitoring the state of a transformer oil is shown, which is also realized in the form of a stick 100. As clearly visible in FIG. 2, stick 100 has a sensor portion 110 comprising an ultrasonic emitter and/or receiver or a resonance chamber 112. Resonance chamber 112 is visible because no protective cover is shown in the alternative configuration of the first embodiment. Additionally, stick 100 has an attachment portion 120 for secure attachment of stick 100 to a transformer, said attachment portion 120 being realized, for example, as a 1.0-inch pipe thread in this alternative. Likewise, a housing 150 is comprised.

FIG. 3 shows an exploded illustration of the alternative configuration of the first embodiment of device 100 according to the disclosure as shown in FIG. 2, FIG. 3 showing the internal structure of device 100. As clearly visible, critical and sensitive components of device 100 are covered and protected by a robust and sophisticated interaction between disposition and housing elements 150, 151 and 152. This stick 100 also has a sensor portion 110 and a resonance chamber 112, which is visible because the protective cover is not illustrated. Furthermore, an acoustic converter 113 and an attachment portion 120 are comprised, the latter, as also shown in FIG. 2, being realized in the form of a 1.0-inch pipe thread, for example.

Furthermore, it is clearly visible in FIG. 3 that a moisture and/or temperature sensor 114 and the resonator are accommodated in resonance chamber 112 and acoustic converter 113. Additionally, the corresponding electronics 115 are comprised. Electronics 115 are surrounded by an insulation 152, which is made of plastic, for example. Housing 150 additionally comprises multiple insulating elements 152, which can be made from plastic, for example. Furthermore, multiple spacer rings 151 and a cable connector 153 are comprised, so as to enable connection to the sensor electronics of stick 100, such as via Modbus.

In FIG. 4, two alternative configurations of a first embodiment of sensor portion 110 of device 100 according to the disclosure are shown. As clearly visible in FIG. 4a and FIG. 4b, sensor portion 110 comprises multiple capacitor plates 116, which are part of a dielectric sensor. Furthermore, a moisture and/or temperature sensor 114 and an acoustic converter having a resonance chamber 113 are comprised. Retaining element 117 can be insulating and can be made of plastic, for example. FIG. 4a additionally illustrates an attachment portion 120, which is realized in the form of a 1.5-inch pipe thread, for example, like in FIG. 1.

FIG. 5 shows a second embodiment of a device 200 according to the disclosure for determining and/or monitoring the state of a transformer oil, said device 200 being realized in the form of a measuring chamber 200. As is clearly visible in FIG. 5, measuring chamber 200 has multiple sensor portions; for instance, a density and/or viscosity sensor 211 and/or an optical sensor 212 are disposed in one sensor portion. In another sensor portion, an acoustic sensor 213 and, furthermore, a dielectric sensor 216 and a moisture and/or temperature sensor 214 are disposed. Moreover, measuring chamber 200 has a housing 250.

In FIG. 6 and FIG. 7, one of the sensor portions 210 of the measuring chamber as shown in FIG. 5 is illustrated in detail. As clearly illustrated in FIGS. 6 and 7, a retaining element 217 is comprised, which is insulating and can be made of plastic, for example. Additionally, capacitor plates 215 (realized as a cylinder capacitor made of concentric tubes) is visible in the two figures, said capacitor plates 215 being part of the dielectric sensor. In FIG. 7, moisture and/or temperature sensor 214 is visible, as well. Furthermore, housing 250, which serves as insulation of the measuring chamber from FIG. 5, as well as cable bushings 251 for connection thereto are visible in FIG. 6 and FIG. 7.

FIG. 8 shows a graphic illustration in the form of a matrix graphic for a calculation example of the determination of the breakdown voltage (BDV) of a transformer oil based on a 2-dimensional function composed of the relative saturation (RS) and of the acoustic disbalance (AcDis). The isogens illustrated in the matrix each correspond to 5 [kV].

In the first stage of the 2-dimensional function, function bdvL (RS, AcDis) is calculated, which depends on main function h(x). In this regard, the following Formula (1) applies:

$$h(x) = \begin{cases} x & \text{if } x \geq 0 \\ 0 & \text{if } x < 0 \end{cases}$$

wherein
h is the main function, and
x is the argument value.

According to Formula (1), the main function has different arguments. If the argument value is x≥0, the function will apply that value. If the argument value is x<0, the value is zero and the term is deleted.

Based on this Formula (1), a calculation example of the determination of the breakdown voltage (BDV) is shown below in Formula (2).

Formula (2) is:

$$bdvL(RS, AcDis) = -0.10 - 0.23h(0.096885 - \log_{10}(RS)) -$$
$$96.79h(\log_{10}(RS) - 0.986885) - 9.38h(\log_{10}(RS) - 1.03756) -$$
$$19.27h(\log_{10}(RS) - 1.43403) + 30.27h(\log_{10}(RS) - 1.51121) +$$
$$0.21h(-0.987312 - \log_{10}(AcDis)) + 67.11h(\log_{10}(AcDis) + 0.987312) -$$
$$169.59h(\log_{10}(RS) - 0.986885) * h(\log_{10}(AcDis) + 1.44532) +$$
$$169.36h(\log_{10}(RS) - 0.986885) * h(-1.44532 - \log_{10}(AcDis)) -$$
$$119.70h(\log_{10}(RS) - 0.986885) * h(\log_{10}(AcDis) + 0.996463) +$$
$$179.58h(\log_{10}(RS) - 0.986885) * h(\log_{10}(AcDis) + 1.99022) +$$
$$0.02h(1.04391 - \log_{10}(RS)) * h(-0.987312 - \log_{10}(AcDis)) +$$
$$13.10h(\log_{10}(RS) - 1.04391) * h(-0.987312 - \log_{10}(AcDis)) +$$
$$11.55h(\log_{10}(RS) - 1.43403) * h(\log_{10}(AcDis) + 2.00147$$

wherein
bdvL is a non-standardized intermediate value of the breakdown voltage,
h is the main function with the argument values x,
wherein
x=RS is the relative saturation, and
x=AcDis is the acoustic disbalance.

In the second stage of the 2-dimensional function, the value bdvL calculated by means of Formula (2) is standardized according to current standard DIN EN 60243-1:2012-05 (cf. "Electrical strength of insulating materials—Test methods—Part 1: Tests at power frequencies" (IEC 112/199/CDV:2011)). Standardizing takes place according to Formula (3):

$$BDV = 10 + \frac{110}{1 + \exp(-bdvL)} [kV]$$

wherein
bdvL is a non-standardized intermediate value of the breakdown voltage, and
BDV is the breakdown voltage.

More information can be found in the known standard work Friedman (1991) Multivariate Adaptive Regression Splines (with discussion) Annals of Statistics 19/1, 1-141, (https://statistics.stanford.edu/research/multivariate-adaptive-regression-splines).

REFERENCE SIGNS 100 stick
110 sensor portion
111 protective cover
112 resonance chamber
113 acoustic converter
114 moisture and/or temperature sensor
115 electronics 116 capacitor plates
117 retaining element
120 attachment portion
150 housing
151 spacer ring
152 insulating element
153 cable connector
200 measuring chamber
210 sensor portion
211 density and/or viscosity sensor
212 optical sensor
213 acoustic sensor
214 moisture and/or temperature sensor
215 capacitor plates
216 dielectric sensor
217 retaining element
250 housing
251 cable bushing

The invention claimed is:

1. A method for determining and/or monitoring a state of a transformer oil, comprising the steps of:
   a) performing an acoustic spectroscopy of the transformer oil, multiple ultrasonic emission signals of different frequencies and/or amplitudes being emitted into the transformer oil and corresponding reflected and/or transmitted ultrasonic reception signals of different frequencies and/or amplitudes being received after having passed through the transformer oil; and
   b) comparing the ultrasonic emission signals with the corresponding ultrasonic reception signals, an n-dimensional function characteristic of the transformer oil being ascertained; and
   c) matching the ascertained characteristic n-dimensional function from step b) with a reference function of corresponding dimension known for transformer oils, selecting a reference transformer oil based on the matching; and
   d) registering a first value of at least one characteristic physical property of the transformer oil; and
   e) comparing the first value with a corresponding value of the reference transformer oil; and
   f) ascertaining the state of the transformer oil based on the comparison performed in step e).

2. The method according to claim 1, wherein the method additionally comprises the step of:
   g) displaying the ascertainment performed in step f).

3. The method according to claim 1, wherein the method comprises an additional step d1) after step d):
   d1) registering at least one second value of the at least one characteristic physical property of the transformer oil.

4. The method according to claim 1, wherein a density, a viscosity, a relative and/or an absolute amount of an inhibitor and/or of an acid of the transformer oil are determined by means of acoustic spectroscopy.

5. The method according to claim 1, wherein the at least one characteristic physical property is a speed of sound, a density, a color, a refractive index, a sound absorption, a temperature, an interfacial tension, a viscosity, a relative and/or absolute saturation, a loss factor, an acid number, an electric constant, an electrical conductivity and/or a concentration of the transformer oil.

6. The method according to claim 1, wherein the state is selected from the list of a remaining useful life, a state of health, a breakdown voltage and/or an imminence of a transformer oil change or of a transformer oil regeneration.

7. A device for determining and/or monitoring the state of a transformer oil according to claim 1, comprising a) a first medium for performing an acoustic spectroscopy of the transformer oil, the first medium comprising an ultrasonic emitter for emitting multiple ultrasonic emission signals of different frequencies and/or amplitudes into the transformer oil and an ultrasonic receiver for receiving corresponding ultrasonic reception signals of different frequencies and/or amplitudes reflected and/or transmitted after having passed through the transformer oil; and
b) a first evaluating unit for comparing the ultrasonic emission signals with the corresponding ultrasonic reception signals, an n-dimensional function characteristic of the transformer oil being ascertained; and
c) a first analyzing unit for matching the ascertained characteristic n-dimensional function from step b) with a reference function of corresponding dimension known for transformer oils to select a reference transformer oil based on the matching; and
d) a second medium for registering a first value of at least one characteristic physical property of the transformer oil; and
e) a second evaluating unit for comparing the first value with a corresponding value of the reference transformer oil; and
f) a second analyzing unit for ascertaining the state of the transformer oil based on the comparison performed in step e).

8. The device according to claim 7, wherein the device additionally comprises an output unit for displaying the ascertainment performed by means of the second analyzing unit.

9. The device according to claim 7, wherein the device comprises an additional medium for registering at least one second value of the at least one characteristic physical property of the transformer oil.

10. The device according to claim 7, wherein the density, the viscosity, the relative and/or absolute amount of an inhibitor and/or of an acid of the transformer oil is determined by means of the first medium.

11. The device according to claim 7, wherein the first medium and/or the second medium register a speed of sound, a density, a color, a refractive index, a sound absorption, a temperature, an interfacial tension, a viscosity, a relative and/or absolute saturation, a loss factor, an acid number, an electric constant, an electrical conductivity and/or a concentration of the transformer oil.

12. The device according to claim 7, wherein the state is selected from a list of remaining useful life, state of health, breakdown voltage and/or imminence of a transformer oil change or of a transformer oil regeneration.

13. The device according to claim 7, wherein the device comprises a heating device.

14. The device according to claim 7, wherein the first medium, the second medium, the first evaluating unit, the second evaluating unit, the first analyzing unit, the second analyzing unit and/or the output unit are disposed in one component.

15. The device according to claim 14, wherein the component is a measuring chamber and/or a stick.

16. A device of high-voltage technology comprising transformer oil and a means for connecting the device to the device according to claim 7, the connection being a direct connection.

17. The device of claim 16, wherein the high-voltage technology comprises a transformer, a capacitor, a Peterson coil, and/or a switch.

* * * * *

UNITED STATES PATENT AND TRADEMARK OFFICE
CERTIFICATE OF CORRECTION

| | | |
|---|---|---|
| PATENT NO. | : 11,353,445 B2 | |
| APPLICATION NO. | : 16/331754 | |
| DATED | : June 7, 2022 | |
| INVENTOR(S) | : Matthias Wrobel | |

It is certified that error appears in the above-identified patent and that said Letters Patent is hereby corrected as shown below:

In the Specification

Column 2, Line 48, "corresponding to ultrasonic" should be --corresponding ultrasonic--.

Signed and Sealed this
Twenty-second Day of November, 2022

Katherine Kelly Vidal
*Director of the United States Patent and Trademark Office*